United States Patent [19]

Schilling et al.

[11] Patent Number: 4,902,715

[45] Date of Patent: Feb. 20, 1990

[54] FUNGICIDAL 4-MONOHALOACETOACETOACETANILIDES

[75] Inventors: Bernd Schilling, Burghausen; Anneliese Reutter, Eglharting; Norman Häberle, Munich, all of Fed. Rep. of Germany

[73] Assignee: The Dow Chemical Company, Midland, Mich.

[21] Appl. No.: 223,199

[22] PCT Filed: Oct. 1, 1987

[86] PCT No.: PCT/EP87/00564

§ 371 Date: Jun. 27, 1988

§ 102(e) Date: Jun. 27, 1988

[87] PCT Pub. No.: WO88/03132

PCT Pub. Date: May 5, 1988

[30] Foreign Application Priority Data

Oct. 28, 1986 [DE] Fed. Rep. of Germany ....... 3636551

[51] Int. Cl.$^4$ .................. C07C 103/34; C07C 122/00; A01N 37/34; A01N 37/18
[52] U.S. Cl. .................................... 514/522; 564/200; 514/628; 558/414
[58] Field of Search ................ 564/200; 514/628, 522; 558/414

[56] References Cited

U.S. PATENT DOCUMENTS 4,552,983 11/1985 Tenud et al. ................. 564/200

FOREIGN PATENT DOCUMENTS 0007089 1/1980 European Pat. Off. ............ 564/200
0088259 9/1983 European Pat. Off. ............ 564/200

OTHER PUBLICATIONS

W. T. Brady et al, "The Reaction of Dimethylketen With Some Acid Halides", J.O.C.S.(C), 1970, pp. 2522-2523.

*Primary Examiner*—John M. Ford
*Assistant Examiner*—Robert C. Whittenbaugh
*Attorney, Agent, or Firm*—S. Preston Jones; Ronald G. Brookens

[57] ABSTRACT

Compounds of the formula

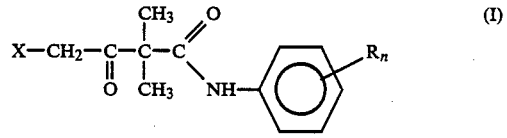

wherein X is a halogen atom, R the same or different substituents in any desired position of the benzene ring, namely, halogen atoms, $C_1$–$C_3$-alkyl groups, trifluoromethyl groups or cyano groups and n a whole number with a value of 1, 2 or 3, are fungicidally active.

2 Claims, No Drawings

FUNGICIDAL 4-MONOHALOACETOACETANILIDES

The invention concerns certain 4-monohalo-2,2-dimethyl-3-oxobutyric acid anilides substituted on the phenyl radical and the use of these compounds as fungicidal-active materials.

The use of 4-chloro-3-oxobutyric acid anilide in seed material disinfection is described by C. H. Arndt (Plant Diseases Reporter 34, p. 334 (1950), correspondingly in Chemical Abstracts, 45, 2129 (1951)). From EP-PS 7 089 (published on the 16th September 1981, N. Haberle et al., Consortium für Elekrochemische Industrie GmbH) is known the use of 2-methylpent-4-enoic acid 3',4'-dichloroanilide and 2-methylbut-3-enoic acid 3',5'-dichloroanilide against spores of Fusarium nivale and Tilletia tritici.

It was the task of the invention to make available fungicides with broader activity spectrum. Furthermore, it was the task of the present invention to make available fungicides which manifest satisfactory action even in the case of small applied amounts. Furthermore, it was the task of the invention to prepare fungicidal-active materials with high compatibility for cultivated plants.

In the scope of the present invention, these tasks are solved by compounds of the formula

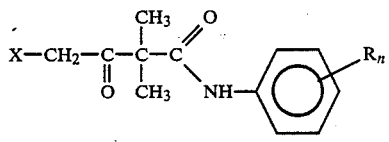

(I)

wherein X is a halogen atom, R the same or different substituents in any desired position of the benzene ring, namely, halogen atoms, $C_1$–$C_3$-alkyl groups, trifluoromethyl groups or cyano groups and n a whole number with a value of 1, 2 or 3.

As residues X, Cl, Br, I, especially Br, are preferred.
As residues R are preferred F, Cl, Br, I, methyl groups, trifluoromethyl groups and cyano groups.

Increasedly effective as fungicides are compounds of the formula (I) in which X stands for a chlorine, bromine or iodine atom and $R_n$ signifies a trifluoromethyl radical in 3-position or, in all, 3 methyl radicals each in the 2, 4 and 6 position.

The compounds of formula (I) according to the invention can be prepared, for example, in that one reacts compounds of the formula

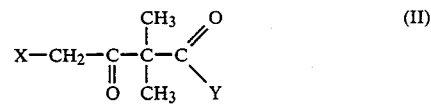

(II)

wherein Y signifies a chlorine or bromine atom, with compounds of the formula

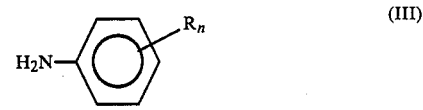

(III)

In the formulae (II) and (III), X, R and n can, in each case, have the same meanings as in formula (I).

The reaction is preferably carried out in the presence of substances binding hydrogen halides, especially in the presence of tertiary amines. Examples of such tertiary amines are tributylamine, N,N-dimethylaniline, pyridine and the like.

The reaction is preferably carried out in a solvent. Examples of suitable solvents are acetic acid ethyl ester, acetone, diethyl ether, dioxan and the like.

In order to suppress side reactions, such as the formation of the corresponding 3,3-dimethylpyrrolidine-2,4-diones, it is recommended to carry out the reaction at relatively low temperature and in the presence of a solvent.

Temperatures of 5° C. to 35° C., especially of 10° C. to 25° C., are preferred. The solvents are preferably used substantially free of water.

Those compounds of the formula (I), in which X signifies an iodine atom, are expediently prepared by Finkelstein reaction from the corresponding compounds of the formula (I), in which X signifies a chlorine or bromine atom, i.e. by reaction with alkali metal iodide in acetone or a solvent of similar properties.

The compounds of formula (II) used as starting materials are obtainable, for example, by the reaction of dimethylketene with alpha-haloacetic acid halides according to DE-OS 33 08 175.

The starting materials of formula (III) are commercially available or can be prepared according to known processes.

In the following Tab. 1 are set out examples of the compounds of formula (I) according to the invention.

TAB. NO. 1

| active material No. | chemical designation | sum formula | melting point in °C. |
|---|---|---|---|
| 1 | 4-chloro-2,2-dimethyl-3-oxo-butyric acid 2'-fluoroanilide | $C_{12}H_{13}ClFNO_2$ | 111 |
| 2 | 4-chloro-2,2-dimethyl-3-oxo-butyric acid 4'-fluoroanilide | $C_{12}H_{13}ClFNO_2$ | 155 |
| 3 | 4-chloro-2,2-dimethyl-3-oxo-butyric acid 2'-(trifluoromethyl)-anilide | $C_{13}H_{13}ClF_3NO_2$ | 69 |
| 4 | 4-chloro-2,2-dimethyl-3-oxo-butyric acid 3'-(trifluoromethyl)-anilide | $C_{13}H_{13}ClF_3NO_2$ | 90 |
| 5 | 4-chloro-2,2-dimethyl-3-oxo-butyric acid 4'-(trifluoromethyl)-anilide | $C_{13}H_{13}ClF_3NO_2$ | 123 |
| 6 | 4-chloro-2,2-dimethyl-3-oxo-butyric acid 4'-cyanoanilide | $C_{13}H_{13}ClN_2O_2$ | 150 |
| 7 | 4-chloro-2,2-dimethyl-3-oxo- | $C_{12}H_{13}ClINO_2$ | 62 |

TAB. NO. 1-continued

| active material No. | chemical designation | sum formula | melting point in °C. |
|---|---|---|---|
| | butyric acid 2'-iodoanilide | | |
| 8 | 4-chloro-2,2-dimethyl-3-oxo-butyric acid 5'-fluoro-2'-methylanilide | $C_{13}H_{15}ClFNO_2$ | 80 |
| 9 | 4-chloro-2,2-dimethyl-3-oxo-butyric acid 3',5'-bis-(trifluoromethyl)-anilide | $C_{14}H_{12}ClF_6NO_2$ | 107 |
| 10 | 4-chloro-2,2-dimethyl-3-oxo-butyric acid 2'-chloro-5'-(trifluoromethyl)-anilide | $C_{13}H_{12}Cl_2F_3NO_2$ | 78 |
| 11 | 4-chloro-2,2-dimethyl-3-oxo-butyric acid 2',3',4'-trimethylanilide | $C_{15}H_{20}ClNO_2$ | 134 |
| 12 | 4-chloro-2,2-dimethyl-3-oxo-butyric acid 2',4',6'-trimethylanilide | $C_{15}H_{20}ClNO_2$ | 110 |
| 13 | 4-chloro-2,2-dimethyl-3-oxo-butyric acid 2',3',4'-trichloroanilide | $C_{12}H_{11}Cl_4NO_2$ | 96 |
| 14 | 4-chloro-2,2-dimethyl-3-oxo-butyric acid 2',4',5'-trichloroanilide | $C_{12}H_{11}Cl_4NO_2$ | 104 |
| 15 | 4-bromo-2,2-dimethyl-3-oxo-butyric acid 4'-fluoro-anilide | $C_{12}H_{13}BrFNO_2$ | 156 |
| 16 | 4-bromo-2,2-dimethyl-3-oxo-butyric acid 4'-methyl-anilide | $C_{13}H_{16}BrNO_2$ | 130 |
| 17 | 4-bromo-2,2-dimethyl-3-oxo-butyric acid 3'-(trifluoromethyl)-anilide | $C_{13}H_{13}BrF_3NO_2$ | 101 |
| 18 | 4-bromo-2,2-dimethyl-3-oxo-butyric acid 2'-chloro-5'-(trifluoromethyl)-anilide | $C_{13}H_{12}BrClF_3NO_2$ | 78 |
| 19 | 4-bromo-2,2-dimethyl-3-oxo-butyric acid 2',4',6'-trimethylanilide | $C_{15}H_{20}BrNO_2$ | 123 |
| 20 | 4-iodo-2,2-dimethyl-3-oxo-butyric acid 4'-fluoro-anilide | $C_{12}H_{13}FINO_2$ | 133 |
| 21 | 4-iodo-2,2-dimethyl-3-oxo-butyric acid 3'-(trifluoromethyl)-anilide | $C_{13}H_{13}F_3INO_2$ | 95 |
| 22 | 4-iodo-2,2-dimethyl-3-oxo-butyric acid 2',4',6'-trimethylanilide | $C_{15}H_{20}INO_2$ | 128* |

*with decomposition.

The compounds according to the invention display fungitoxic properties. They are used against fungal attacks on plants or on plant products.

Depending upon the phenyl substitution, there are thereby achieved actions against *Botrytis cinerea*, against fungal spores in general, against rust fungi (e.g. bean rust=Uromyces phaseoli), against oomycetes, such as e.g. *Phytophthora infestans, Plasmopara viticola*, or *Pythium ultimum* or against Ascomycetes, such as e.g. *Venturia inaequalis* (=apple scab). *Piricularia oryzae* (leaf spot disease in rice) is also combatable with a part of the compounds according to the invention.

The active materials according to the invention are suitable, without their field of use thereby being restricted thereto, e.g. for use in viticulture, in horticulture and vegetable cultivation (especially salad cultivation and strawberry cultivation), in cereal production, in rape production, in hop production, and in stoned fruit production. On the other hand, the compounds according to the invention are not suitable for the combating of types of mildew, such as e.g. *Erysiphe cichoracearum* (mildew in gherkins) or cereal mildew (*Erysiphe graminis*).

The application of the active materials takes place in per se known manner to the living area of the fungi, for example by pouring, splashing, spraying, dusting, coating. There can be achieved not only a prophylactic but also a curative action.

The active materials according to the invention can be applied alone or in admixture with other pesticides, especially fungicidal agents. In general, they are used as mixtures with solid or liquid dilution agents or as solutions in solid or liquid solvents with active material contents of 0.005 to 95 wt.%.

In general, the mixtures or solutions are prepared as emulsion concentrates, pastes, spray powders, granulates or microcapsules.

In general, emulsion concentrates and pastes contain 10 to 90 wt.%, preferably 15 to 50 wt.% of active material, 2 to 25 wt.% of dispersion adjuvants and organic solvents and/or water.

Spray powders mostly contain 10 to 80 wt.%, preferably 15 to 70 wt.% of active material, 1 to 30 wt.% of dispersion adjuvants and 10 to 89 wt.% of inert components.

Besides inert components and/or coating materials, granulates and microcapsules contain 1 to 10 wt.%, preferably 5 to 10 wt.% of active material.

According to the invention, there are used: as dispersion adjuvants, e.g. alkyl and aryl sulphonates, methyl cellulose, polymeric sulphonic acids and their salts, polyalcohols, fatty acid esters, fatty alcohol ethers, fatty amines;

as organic solvents, e.g. alcohols, such as ethanol, butanols, dimethylformamide, dimethyl sulphoxide, N-methylpyrrolidione, aromatics, such as toluene and xylenes;

as inert components, e.g. kaolin, China clay, talc, calcium carbonate, highly dispersed silicic acid, silica gels, kieselguhr, diatomaceous earth, pumice, brick dust, coarse-ground maize, thickening agents, such as starch and carboxymethylcellulose, cyclodextrins;

as binding agents, e.g. magnesium sulphate, gypsum, gum arabic, polyvinyl alcohol.

For example, for use as fungicides, the active materials according to the invention are formulated as follows:

| Spray powder | |
|---|---|
| 20 wt. % | active material |
| 44 wt. % | China clay |
| 16 wt. % | highly dispersed silicic acid |
| 15 wt. % | lignin sulphonate (cell pitch) |
| 5 wt. % | sodium alkylnaphthalenesulphonate-formaldehyde condensate (Atlox 4862, Registered Trade Mark, manufacturer: Atlas-Chemie, D-4300 Essen) |

| Emulsion concentrate | |
|---|---|
| 20 wt. % | active material |
| 30 wt. % | cyclohexanone |
| 30 wt. % | xylene |
| 20 wt. % | Tween Twenty (Registered Trade Mark, manufacturer Atlas-Chemie, D-4300 Essen). |

The following Examples serve for the explanation of the invention. The products according to the invention were, in each case, identified by $^1$H-NMR spectroscopy (inner standard: tetramethylsilane).

EXAMPLE 1, PREPARATION EXAMPLE
4-Chloro-2,2-dimethyl-3-oxobutyric acid 3'-(trifluoromethyl)-anilide, active material 4

18.3 g. (0.1 mole) 4-chloro-2,2-dimethyl-3-oxobutyric acid chloride were dissolved in 150 ml. acetic acid ethyl ester and a mixture of 16.1 g. (0.1 mole) 3-trifluoromethylaniline, 10.1 g. (0.1 mole) triethylamine and 50 ml. acetic acid ethyl ester added dropwise thereto, with stirring, at 20° C. within 90 min. Subsequently, for the completion of the reaction, it was further stirred for 60 min. at 35° C., then the solvent distilled off, 100 ml. cyclohexane added thereto and the still warm mixture filtered. From this filtrate, the desired product crystallised out.

Yield: 27.8 g. (90.4% of theory); melting point: 69° C. $^1$H-NMR (CDCl$_3$): 1.6 ppm (s, 6H, 2 CH$_3$ groups in 2-position of the acyl radical), 4.4 ppm (s, 2H, CH$_2$ group of the acyl radical), 7.2–7.85 ppm (m, 4H, 4 arom. protons), 8.0 ppm (s, 1H, broad, NH).

EXAMPLE 2, PREPARATION EXAMPLE
4-Iodo-2,2-dimethyl-3-oxobutyric acid 3'-(trifluoromethyl)-anilide, active material 21

22 g. (0.07 mole) of the 4-chloro derivative prepared according to Example 1 were dissolved in 15 ml. dry acetone and a solution of 10.5 g. (0.07 mole) sodium iodide in acetone added thereto. The mixture was heated to reflux for 7 hrs., then cooled and the sodium chloride formed filtered off. The filtrate was evaporated and the residue crystallised. By recrystallisation from methanol/water (4:1), the desired substance was obtained in 74.9% yield. The melting point of the compound lay at 95° C.

$^1$H-NMR (CDCl$_3$) 1.6 ppm (s, 6H, 2 CH$_3$ groups in 2-position of the acyl radical), 4.1 ppm (3, 2H, CH$_2$ group of the acyl radical), 7.15–7.9 ppm (m, 4H, 4 arom. protons), 8.1 ppm (s, 1H broad, NH).

For the following working examples, some of the known acylanilides were used as comparative agents:

1. 4-chloro-3-oxobutyric acid anilide, e.g. known from C. H. Arndt, Plant Diseases Reptr. 34, 334–347 (1950) C.A. 45, 2129t, 1951), in the following referred to as "comparison A", 2. 3-oxobutyric acid 3',4'-dichloroanilide, known as herbicide from CH 542,575, in the following referred to as "comparison B", 3. 2-methylpent-4-enoic acid 3'-chloro-4'-methyl-anilide, known from EP 7.089, in the following referred to as "comparison C", 4. 2,2-dimethylpent-4-enoic acid 3',4'-dichloroanilide, also known from EP 7.089, in the following referred to as "comparison D".

EXAMPLE 3, WORKING EXAMPLE

Spore germ test

50 μl. of a solution or suspension of an active material with a content of 250 ppm of active substance were, together with 50 μl. of a spore suspension, produced by slurrying of spores from an agar culture with a nutrient solution which, per litre, contained 10 g. sugar, 1 g. glycol, 1 g. KH$_2$PO$_4$ and 0.5 g. MgSO$_4$, introduced into the hollow cut-out of a hollow cut-out object slide. The object slide was stored at 20° C. for 48 hours in a Petri dish, the bottom of which was covered with moistened filter paper.

Thereafter, the ratio of the germinated and of the non-germinated spores was compared against an untreated control sample. The degree of action is given in % according to the following formula:

$$100 - \frac{\text{number of germinated spores, treated}}{\text{number of germinated spores, untreated}} \times 100$$

The results are summarised in the following Tab. 2.

TAB. NO. 2

| | Fungitoxicity of active materials according to the invention and of comparative agents at 250 ppm active material concentration in % | | | | | | |
|---|---|---|---|---|---|---|---|
| Active material No. | Alternaria solani | Botrytis cinerea | Fusarium colmorum | Fusarium nivale | Colletotrichum coffeanum | Verticillium dahliae | Penicillium glaucum |
| 1 | 20 | 80 | 20 | 80 | 80 | 10 | 0 |
| 3 | 95 | 90 | 70 | 100 | 100 | 100 | 60 |
| 4 | 60 | 80 | 80 | 100 | 100 | 80 | 70 |
| 6 | 80 | 100 | 80 | 80 | 100 | 80 | 80 |
| 7 | 20 | 80 | 80 | 80 | 100 | 100 | 80 |
| 8 | 100 | 100 | 100 | 100 | 100 | 100 | 100 |

TAB. NO. 2-continued

Fungitoxicity of active materials according to the invention and of comparative agents at 250 ppm active material concentration in %

| Active material No. | Alternaria solani | Botrytis cinerea | Fusarium colmorum | Fusarium nivale | Colletotrichum coffeanum | Verticillium dahliae | Penicillium glaucum |
|---|---|---|---|---|---|---|---|
| 10 | 60 | 90 | 100 | 100 | 100 | 100 | 100 |
| 11 | 30 | 100 | 20 | 100 | 100 | 100 | 100 |
| 13 | 100 | 100 | 90 | 100 | 100 | 100 | 100 |
| 14 | 100 | 100 | 100 | 100 | 100 | 100 | 100 |
| 15 | 10 | 100 | 100 | 100 | 100 | 100 | 30 |
| 16 | 95 | 100 | 100 | 100 | 100 | 100 | 100 |
| 17 | 100 | 100 | 100 | 100 | 100 | 100 | 100 |
| 18 | 80 | 100 | 80 | 100 | 100 | 100 | 10 |
| 19 | 60 | 100 | 70 | 100 | 100 | 100 | 10 |
| 21 | 100 | 100 | 100 | 100 | 100 | 100 | 100 |
| 22 | 30 | 80 | 30 | 100 | 100 | 100 | 10 |
| comparsion A | 0 | 0 | 20 | 100 | n.d.* | 0 | n.d.* |
| comparison B | 0 | 0 | 10 | 80 | n.d.* | 10 | n.d.* |
| comparison C | 0 | 10 | 0 | 100 | 0 | 0 | 0 |
| comparison D | 0 | 10 | 0 | 10 | 10 | 20 | 0 |

*n.d. = not determined

EXAMPLE 4, WORKING EXAMPLE

Grape juice test 20 ml. of a nutrient solution of grape juice and distilled water in the ratio of 1:1 were filled into Petri dishes and mixed with the active materials given in the following Table. The active material concentration amounted to 31 ppm. Subsequently, the experimental batches were, in each case, inoculated with 50 μl. of a Botrytis spore suspension, produced by slurrying of the Botyrtis spores from an agar culture with distilled water.

After a culturing period of 10 or 20 days at 20° C., the extent of the fungus development on the nutrient solution surface was assessed.

The degree of action was calculated in % according to the following formula:

$$100 - \frac{\text{fungus growth, treated}}{\text{fungus growth, untreated}} \times 100$$

TAB. NO. 3

Effectiveness of compounds according to the invention and of comparative agents in % degrees at 31 ppm active material concentration after 10 or 20 days period of action

| Active material No. | % Effectiveness after 10 days | after 20 days |
|---|---|---|
| 8 | 100 | 100 |
| 10 | 100 | 100 |
| 11 | 100 | 100 |
| 12 | 100 | 80 |
| 13 | 100 | 100 |
| 14 | 100 | 100 |
| 15 | 100 | 100 |
| 16 | 100 | 100 |
| 17 | 100 | 100 |
| 18 | 100 | 100 |
| 19 | 100 | 100 |
| 20 | 100 | 100 |
| 21 | 100 | 100 |
| 22 | 90 | 70 |
| comparison A | 0 | 0 |
| comparison C | 0 | 0 |
| comparison D | 0 | 0 |

Especially active compounds according to the invention, such as e.g. 13, 14, 15, 16, 18 and 20, still showed 100% effectiveness even at 8 ppm active material concentration.

EXAMPLE 5, WORKING EXAMPLE

Effectiveness against Pythium ultimum in the case of soil application.

The active material was uniformly mixed in a concentration of 500 ppm with soil which has been artificially infected with Pythium ultimum. The so treated soil was filled into plastic pots (in each case 4 repetitions per test substance) and each seeded with 10 pea seeds. These pots were kept for 10 days at 24 to 26° C. and at an atmospheric humidity of 75 to 90%. Thereafter, the number of healthy, germinated plants was determined. The degree of action was calculated by comparison with infected but untreated soil samples. The results are summarised in the following Table.

TAB. NO. 4

Effectiveness of active materials according to the invention and of comparative agents in % degrees at 500 ppm active material concentration against Pythium ultimum.

| Active material No. | % effectiveness |
|---|---|
| 1 | 80 |
| 2 | 80 |
| 3 | 100 |
| 4 | 100 |
| 5 | 100 |
| 8 | 80 |
| 11 | 80 |
| 19 | 80 |
| comparison A | 20 |
| comparison B | 0 |
| comparison C | 25 |
| comparison D | 20 |

EXAMPLE 6, WORKING EXAMPLE

Effectiveness against Uromyces phaseoli (bean rust)

Young bean plants which had formed the first three-leaf sprouting (14-18 days after sowing) were sprayed dripping wet with a formulation of the active material to be tested (active material concentration 500 ppm). About 20 hours after the spraying, when the spray coating is completely dried, the plants were artificially uniformly infected with a spore suspension of Uromyces phaseoli which had been obtained from infected bean plants.

After remaining for 20-24 hours in a dark humid chamber (18°—22° C.; 90-100% atmospheric humidity), the test plants were kept in a greenhouse at 18°-22°

C. and 60-80% atmospheric humidity for two weeks. Subsequently, when untreated control plants showed strong attack, the degree of attack of the test plants was ascertained.

TAB. NO. 5

Effectiveness of active materials according to the invention and of comparative agents against *Uromyces phaseoli* (bean rust) at 125 ppm active material concentration.

| Active material No. | % effectiveness |
| --- | --- |
| 1 | 100 |
| 2 | 55 |
| 3 | 90 |
| 4 | 95 |
| 9 | 85 |
| 10 | 80 |
| 11 | 80 |
| 12 | 80 |
| 19 | 90 |
| comparison A | 50 |
| comparison B | 0 |
| comparison C | 10 |
| comparison D | 15 |

We claim:

1. Compounds of the formula

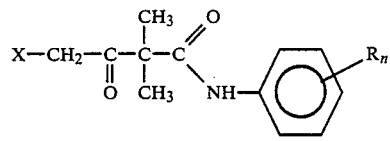

wherein X is a chlorine, bromine or iodine atom, each R is the same or different substituents in any desired ring position of the benzene ring, and is namely, halogen atoms, $C_1$–$C_3$-alkyl groups, trifluoromethyl groups or cyano groups and ? is a whole number with a value of 1, 2 or 3.

2. A method for killing and controlling fungi which attack plants or plant products which comprises applying to the fungi or its living area an amount of a composition effective to kill and/or control said fungi, said composition comprising, as the fungicidal-active material, a compound of the formula

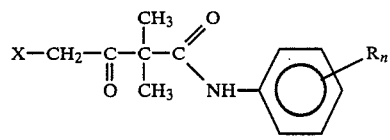

wherein X is a chlorine, bromine or iodine atom, each R is the same or different substituents in any desired ring position of the benzene ring, and is namely, halogen atoms, $C_1$–$C_3$-alkyl groups, trifluoromethyl groups or cyano groups and n is a whole number with a value of 1, 2 or 3 in admixture with inert adjuvants.

* * * * *